US010520457B2

(12) United States Patent
Santangelo et al.

(10) Patent No.: US 10,520,457 B2
(45) Date of Patent: Dec. 31, 2019

(54) SENSOR OF VOLATILE SUBSTANCES WITH INTEGRATED HEATER AND PROCESS FOR MANUFACTURING A SENSOR OF VOLATILE SUBSTANCES

(71) Applicant: STMICROELECTRONICS S.R.L., Agrate Brianza (IT)

(72) Inventors: Antonello Santangelo, Belpasso (IT); Salvatore Cascino, Gravina di Catania (IT); Roberto Modica, Mascalucia (IT); Viviana Cerantonio, Acireale (IT); Maurizio Moschetti, Gravina di Catania (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 0 days.

(21) Appl. No.: 15/836,587

(22) Filed: Dec. 8, 2017

(65) Prior Publication Data
US 2018/0100825 A1 Apr. 12, 2018

Related U.S. Application Data

(63) Continuation of application No. 14/611,062, filed on Jan. 30, 2015, now Pat. No. 9,841,393.

(30) Foreign Application Priority Data

Jan. 31, 2014 (IT) .............................. TO2014A0075

(51) Int. Cl.
*G01N 27/22* (2006.01)
(52) U.S. Cl.
CPC ............ *G01N 27/225* (2013.01); *G01N 27/22* (2013.01); *G01N 27/223* (2013.01); *G01N 27/227* (2013.01)

(58) Field of Classification Search
CPC .... G01N 27/225; G01N 27/22; G01N 27/223; G01N 27/227
See application file for complete search history.

(56) References Cited

U.S. PATENT DOCUMENTS

| 5,296,819 A | 3/1994 | Kuroiwa et al. |
| 6,356,087 B1 | 3/2002 | Wallrafen |

(Continued)

FOREIGN PATENT DOCUMENTS

| DE | 3911812 A1 | 10/1990 |
| DE | 102 46 050 A1 | 4/2004 |

(Continued)

OTHER PUBLICATIONS

Gu et al., "A novel capacitive-type humidity sensor using CMOS fabrication technology," *Sensors and Actuators B* 99:491-498, 2004.

(Continued)

*Primary Examiner* — David Z Huang
(74) *Attorney, Agent, or Firm* — Seed Intellectual Property Law Group LLP

(57) ABSTRACT

A sensor of volatile substances including: a sensitive layer, of a sensitive material that is permeable to a volatile substance and has an electrical permittivity depending upon a concentration of the volatile substance absorbed; a first electrode structure and a second electrode structure capacitively coupled together and arranged so that a capacitance between the first electrode structure and the second electrode structure is affected by the electrical permittivity of the sensitive material; and a supply device, configured to supply a heating current through one between the first electrode structure and the second electrode structure in a first operating condition, so as to heat the sensitive layer.

12 Claims, 12 Drawing Sheets

(56) References Cited

U.S. PATENT DOCUMENTS

| | | | |
|---|---|---|---|
| 6,690,569 | B1 | 2/2004 | Mayer et al. |
| 6,787,047 | B1 | 9/2004 | Hahn et al. |
| 9,164,052 | B1 | 10/2015 | Speer et al. |
| 2004/0080325 | A1 | 4/2004 | Ogura |
| 2009/0261845 | A1 | 10/2009 | Hierlemann et al. |
| 2010/0134948 | A1 | 6/2010 | Park et al. |
| 2010/0147070 | A1 | 6/2010 | Jun et al. |
| 2012/0304742 | A1 | 12/2012 | Cummins |
| 2013/0049212 | A1 | 2/2013 | Hata et al. |
| 2013/0187670 | A1 | 7/2013 | Dooley et al. |
| 2014/0077314 | A1 | 3/2014 | Humbert et al. |
| 2014/0139241 | A1 | 5/2014 | Sakai et al. |
| 2014/0151538 | A1 | 6/2014 | Syed et al. |

FOREIGN PATENT DOCUMENTS

| | | |
|---|---|---|
| EP | 1 387 164 A1 | 2/2004 |
| EP | 2 508 874 A1 | 10/2012 |

OTHER PUBLICATIONS

Kang et al., "A High-Speed Capacitive Humidity Sensor with On-Chip Thermal Reset," *IEEE Transactions on Electron Devices* 47(4):702-710, Apr. 2000.

Kim et al., "High Sensitivity Capacitive Humidity Sensor with a Novel Polyimide Design Fabricated by MEMS Technology," Proceedings of the 2009 4$^{th}$ IEEE International Conference on Nano/Micro Engineered and Molecular Systems, Jan. 5-8, 2009, Shenzhen, China, pp. 703-706.

Laconte et al., "Capacitive Humidity Sensor Using a Polyimide Sensing Film," Design, Test, Integration & Packaging of MEMS/MEMS, Cannes-Mandelieu, May 5-7, 2003, pp. 223-228.

Melcher et al., "Dielectric Effects of Moisture in Polyimide," *IEEE Transactions on Electrical Insulation* 24(1):31-38, Feb. 1989.

Patel et al., "Chemicapacitive microsensors for detection of explosives and TICs," *Proceedings of the SPIE; Unmanned/Unattended Sensors and Sensor Networks II* 5986:162-171, 2005.

Saikumar et al., "Time Lag and Permeation in Multilayer Polymer Coatings," *IEEE Transactions on Components, Hybrids, and Manufacturing Technology* 16(5):517-522, Aug. 1993.

Schubert et al., "A Polyimide-Based Capacitive Humidity Sensor," *IEEE Transactions on Electron Devices* ED-32(7):1220-1223, Jul. 1985.

Wang et al., "A Low-Cost Capacitive Relative Humidity Sensor for Food Moisture Monitoring Application," 4$^{th}$ Asia Symposium on Quality Electronic Design, Penang, Malaysia, Jul. 10-11, 2012, pp. 95-99.

Zeng et al., "Fabrication and Test of MEMS/NEMS based Polyimide Integrated Humidity, Temperature and Pressure Sensor," Proceedings of the 1$^{st}$ IEEE International Conference on Nano/Micro Engineered and Molecular Systems, Jan. 18-21, 2006, Zhuhai, China, pp. 788-791.

Zhao et al., "A Fully Packaged CMOS Interdigital Capacitive Humidity Sensor With Polysilicon Heaters," *IEEE Sensors Journal* 11(11):2986-2992, Nov. 2011.

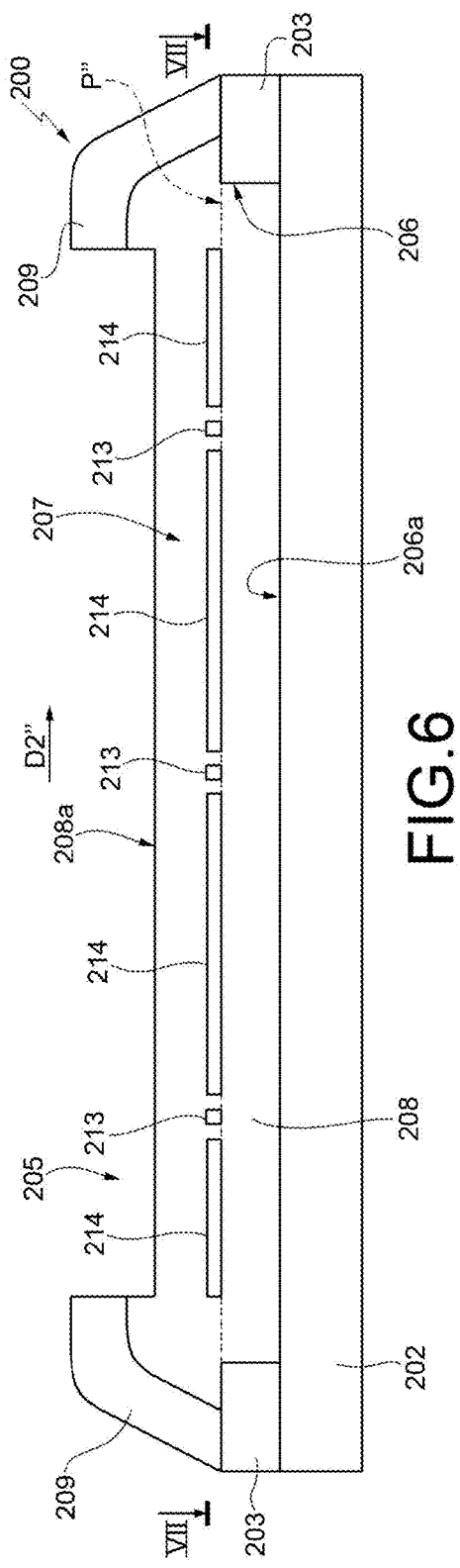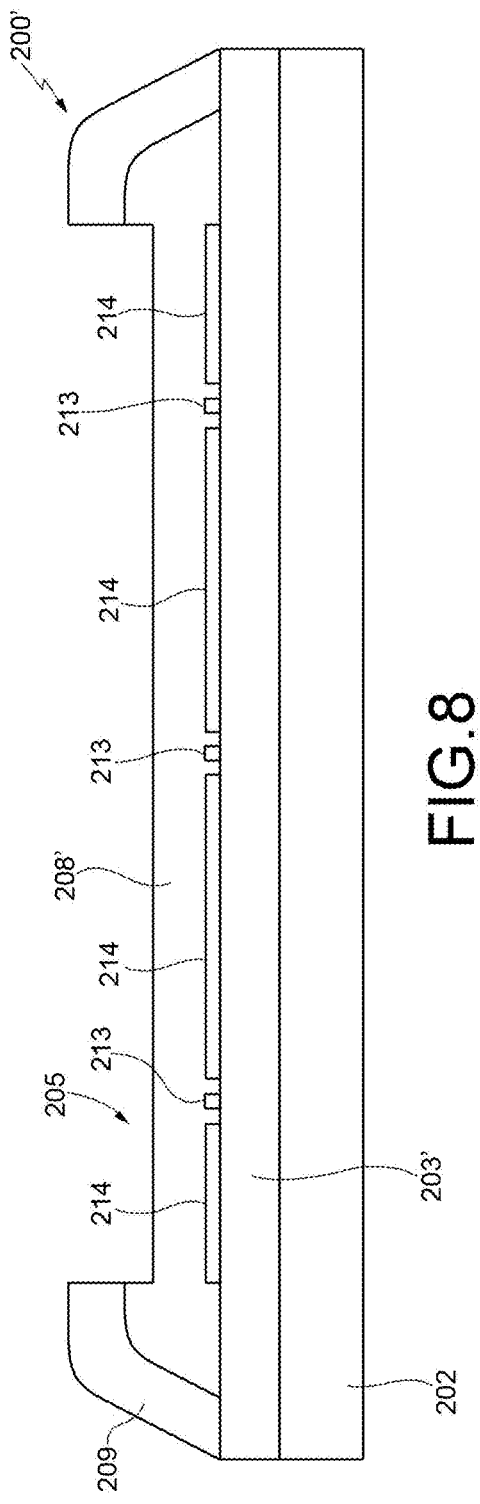

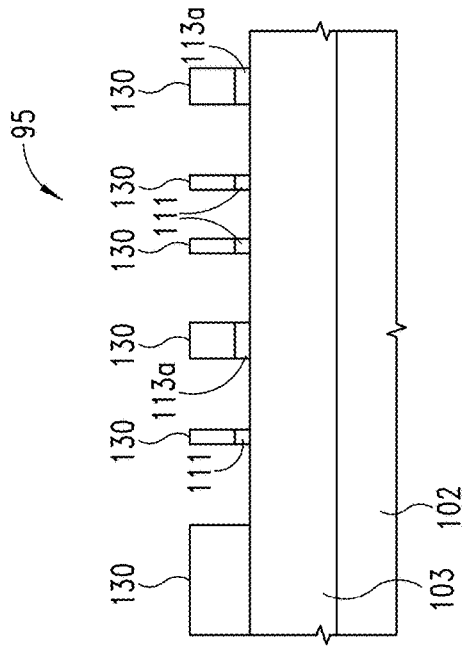
FIG.10
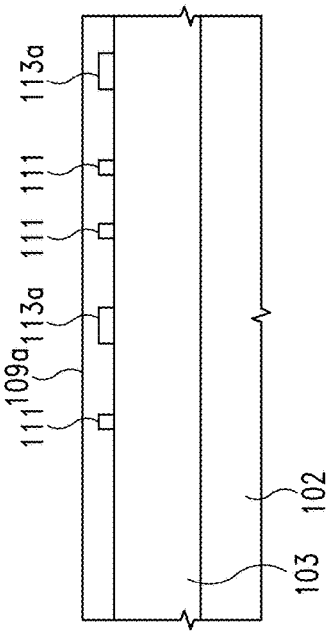
FIG.11
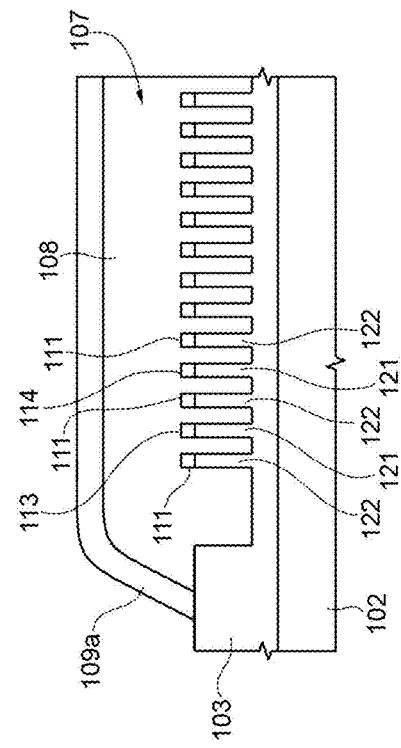
FIG.12
FIG.13

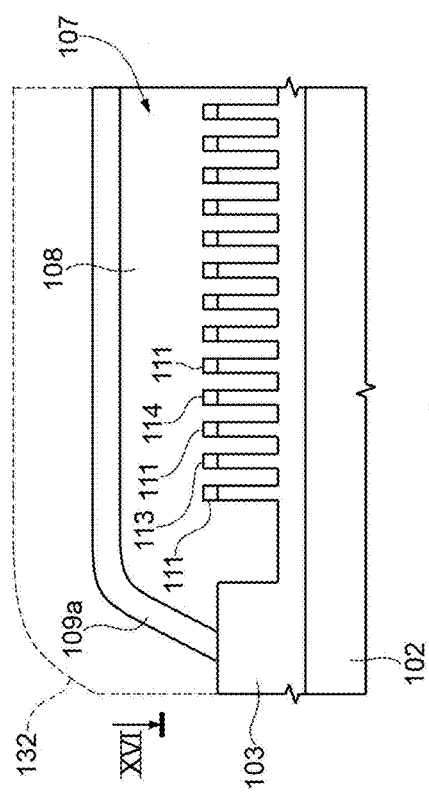
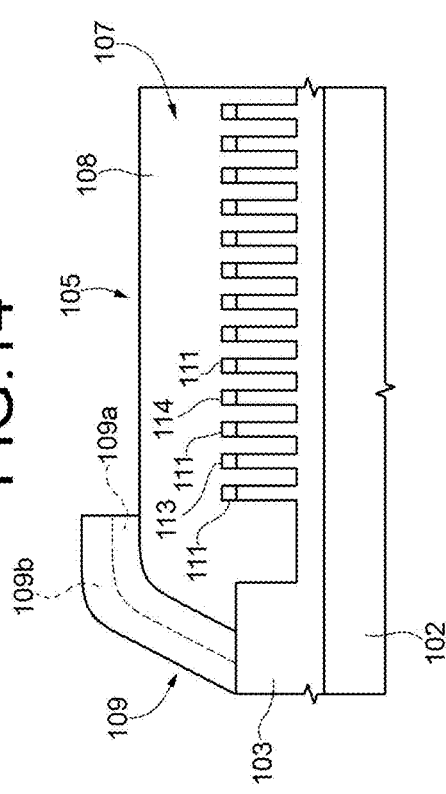
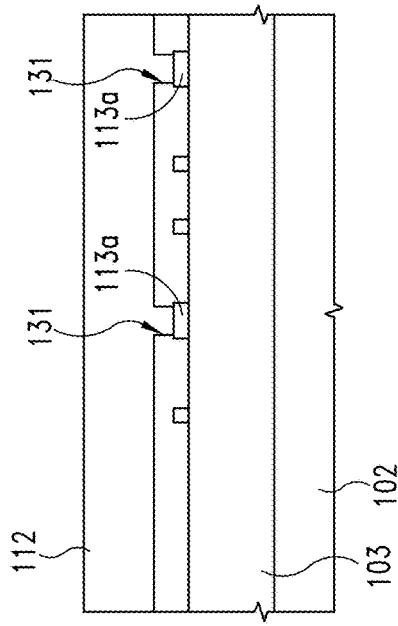
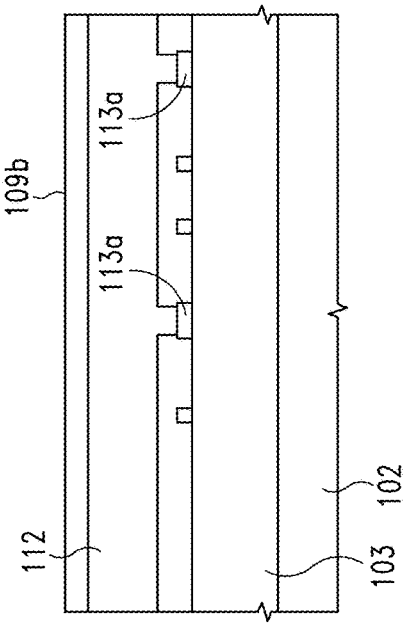
FIG.14
FIG.17
FIG.15
FIG.18

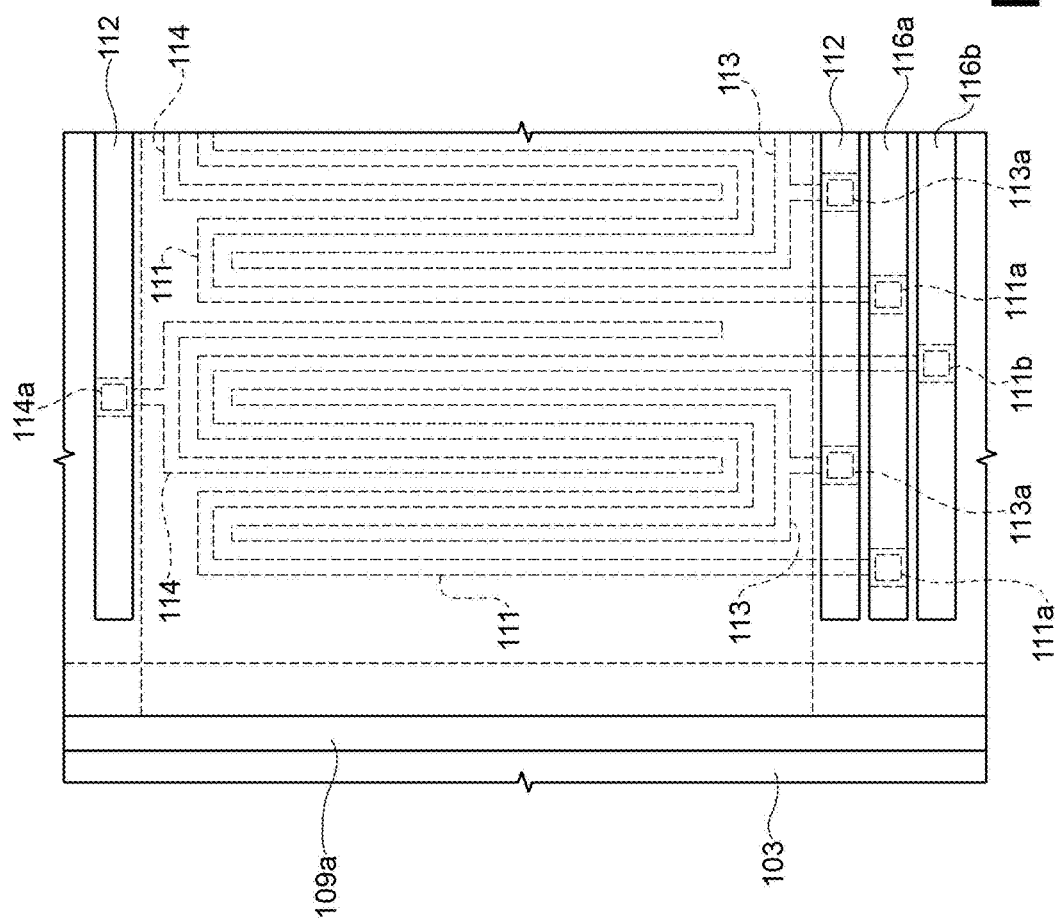

SENSOR OF VOLATILE SUBSTANCES WITH INTEGRATED HEATER AND PROCESS FOR MANUFACTURING A SENSOR OF VOLATILE SUBSTANCES

BACKGROUND

Technical Field

The present disclosure relates to a sensor of volatile substances with an integrated heater and to a process for manufacturing a sensor of volatile substances.

Description of the Related Art

Known to the art are humidity sensors of a capacitive type, which exploit as sensitive materials particular hygroscopic dielectric materials having an electrical permittivity that varies as a function of the degree of relative humidity. In practice, a sensitive layer of hygroscopic dielectric material is set between conductive structures coupled for forming the electrodes of a capacitor. The capacitance of the capacitor notoriously depends upon the electrical permittivity of the material that is present between the electrodes. Since this varies according to the humidity absorbed by the sensitive layer, the reading of the capacitance of the capacitor supplies a measurement of the level of relative humidity in the environment.

Capacitive humidity sensors are much appreciated for their high sensitivity, good linearity over a wide range of values of relative humidity, low consumption, ease of miniaturization, and low manufacturing costs.

Some known types of capacitive humidity sensors use capacitors with plane and parallel plates. In this case, the electrodes of the capacitor are defined by parallel plates, and the sensitive layer is contained in a volume comprised between the electrodes. One of the electrodes of the capacitor, the external one, has through openings for enabling the environmental humidity to impregnate the sensitive layer. A limit of sensors of this type is represented by the response time, which is rather slow. In fact, the exposed surface of the sensitive layer is small and is limited to the areas corresponding to the openings of the external electrode, which, on the other hand, cannot be increased beyond a certain limit without affecting the overall capacitance of the sensor.

Also sensors based upon comb-shaped and comb-fingered capacitive structures have been proposed. In this case, two comb-shaped, comb-fingered, and coplanar electrodes are formed on a planar dielectric substrate and then coated with a sensitive layer of hygroscopic dielectric material, the electrical permittivity of which varies as a function of the humidity absorbed.

Capacitive humidity sensors may present undesirable phenomena of hysteresis. In fact, when the relative humidity decreases, the hygroscopic dielectric material takes a rather long time, longer than the time taken for absorption, to release the water molecules absorbed.

For this reason, humidity sensors may incorporate heaters thermally coupled to the layer of hygroscopic dielectric material. The heaters enable faster release of the humidity absorbed and thus improvement of the response of the sensors.

A heater may comprise conductive strips, for example of doped polysilicon, and is in general provided in a region underlying the detection electrodes. For instance, the heater may be provided on a substrate and incorporated into an insulating layer on which the detection electrodes are set, which are in turn coated with the layer of hygroscopic dielectric material.

To prevent any electrical contact between the heater and the detection electrodes, the insulating layer should have a certain thickness. This thickness, however, tends to reduce also the thermal coupling between the heater and the hygroscopic dielectric material and thus represents a limit for the performance of the humidity sensor.

BRIEF SUMMARY

One embodiment of the present disclosure is directed to a sensor of volatile substances that includes a substrate, a sensitive layer on the substrate, the sensitive layer being of a sensitive material that is permeable to a volatile substance and has electric permittivity dependent on a concentration of the volatile substance absorbed by the sensitive material, a first electrode structure and a second electrode structure that are coplanar in a same plane and capacitively coupled to each other and arranged so that a capacitance between the first electrode structure and the second electrode structure is affected by the electric permittivity of the sensitive material, and a supply device, configured to supply a heating current through one of the first electrode structure and the second electrode structure in a first operating condition, so as to heat the sensitive layer.

BRIEF DESCRIPTION OF THE SEVERAL VIEWS OF THE DRAWINGS

For a better understanding of the disclosure, some embodiments thereof will now be described, purely by way of non-limiting example and with reference to the attached drawings, wherein:

FIG. 6 is a cross-section through a sensor of volatile substances according to a different embodiment of the present disclosure;

FIG. 8 is a cross-section through a sensor of volatile substances according to a further embodiment of the present disclosure;

FIG. 10 is a cross-section of the sensor of FIG. 9, taken along the plane X-X of FIG. 9;

FIG. 11 is a cross-section of the sensor of FIG. 9, taken along the plane XI-XI of FIG. 9;

FIG. 12 shows the view of FIG. 10 in a subsequent machining step;

FIG. 13 shows the view of FIG. 11 in a subsequent machining step;

FIG. 14 shows the view of FIG. 12 in a subsequent machining step;

FIG. 15 shows the view of FIG. 13 in a subsequent machining step;

FIG. 16 is a simplified top plan view, with parts removed for reasons of clarity, of the wafer of FIG. 14, sectioned along the plane XVI-XVI of FIG. 14;

FIG. 17 shows the view of FIG. 14 in a subsequent machining step; and

FIG. 18 shows the view of FIG. 15 in a subsequent machining step.

DETAILED DESCRIPTION

Figure 1:
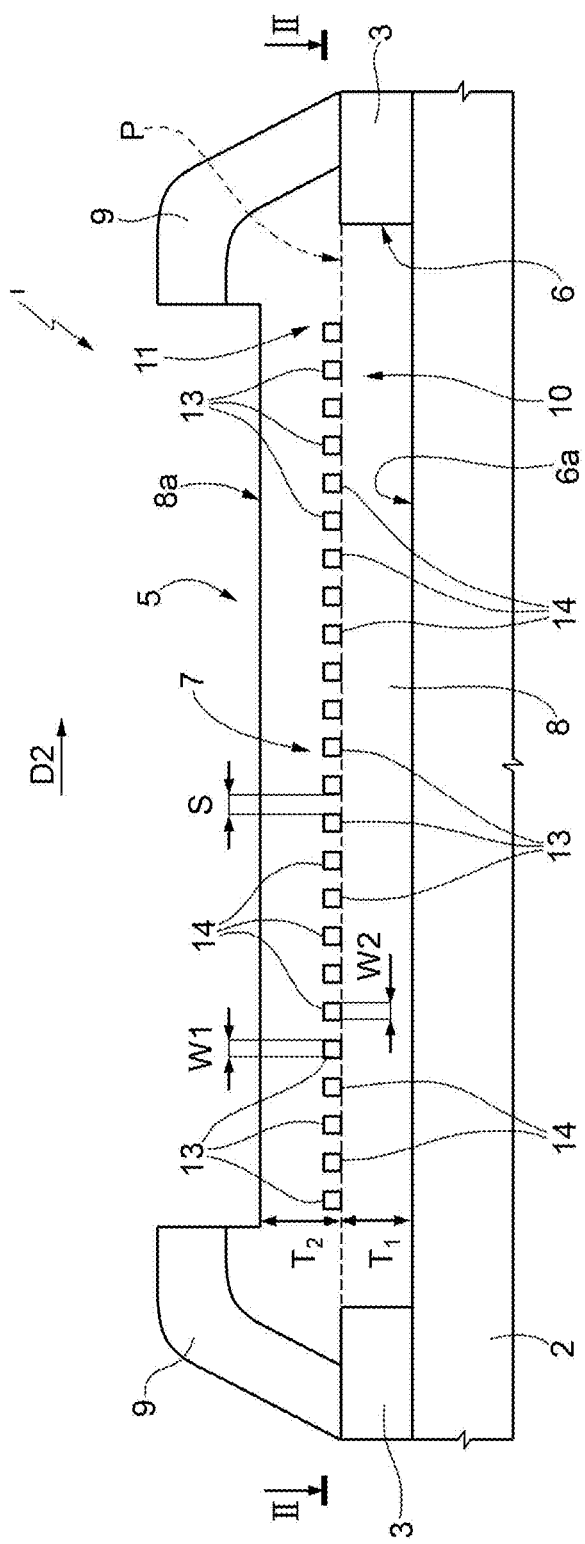
FIG. 1 is a cross-section through a sensor of volatile substances according to one embodiment of the present disclosure.
Figure 2:
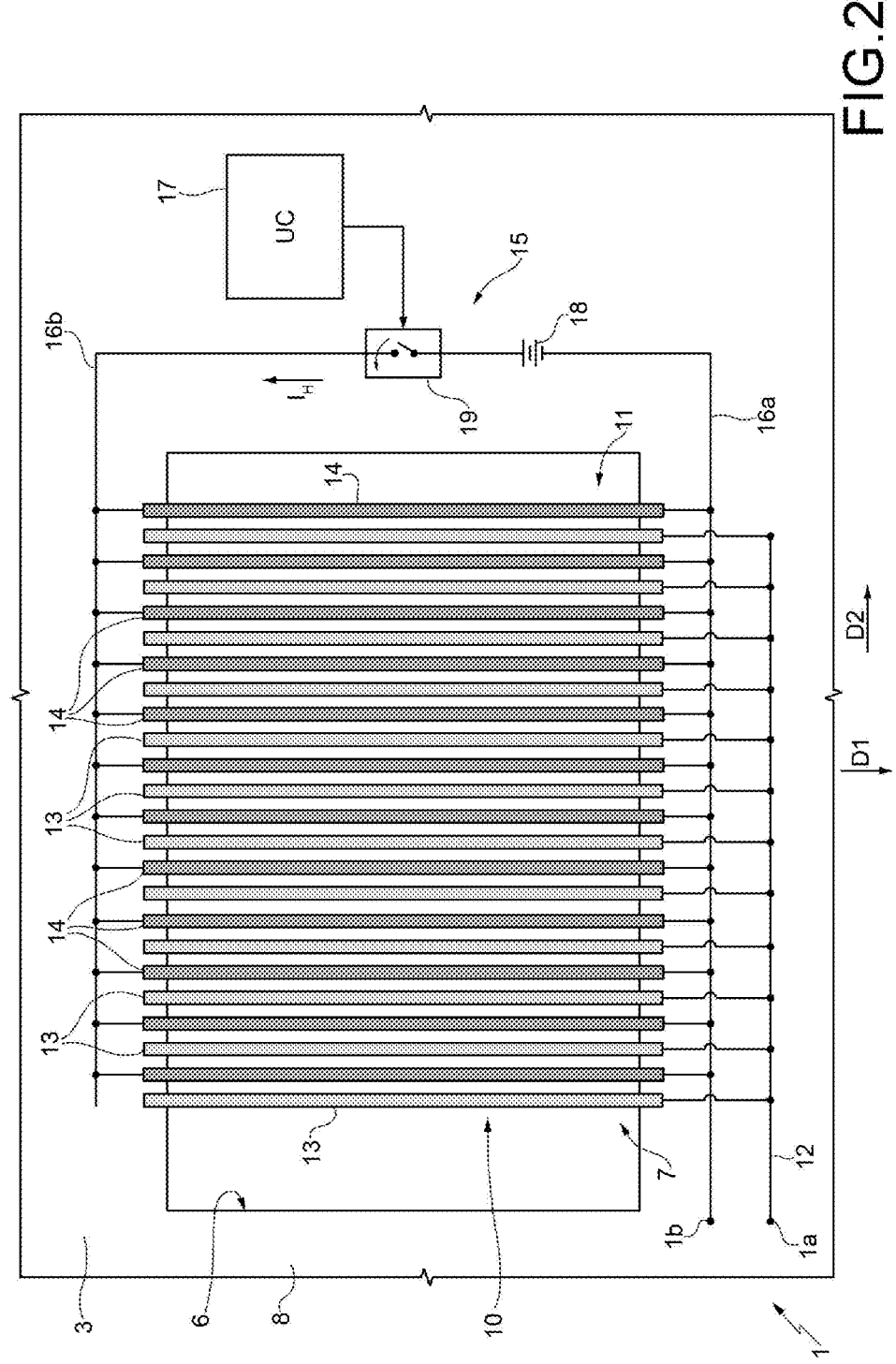
FIG. 2 is a simplified top plan view, with parts removed for reasons of clarity, of the sensor of FIG. 1, sectioned along the plane II-II of FIG. 1.

With reference to FIGS. 1 and 2, a sensor of volatile substances, in the case in point a humidity sensor, is designated as a whole by the number 1.

The sensor 1 is of a capacitive type and uses as sensitive material a hygroscopic polymer the electrical permittivity of which varies as a function of the humidity absorbed.

In detail, the sensor 1 comprises a substrate 2, for example of silicon, on which a structural layer 3 of dielectric material, for example silicon oxide, is provided.

The substrate 2 defines a supporting layer for the structural layer 3 and the other structures described hereinafter.

The structural layer 3 has a through cavity 6, the bottom 6a of which is defined by a surface of the underlying layer, in this case the substrate 2.

The sensor 1 further comprises a sensing structure 7, which, in one embodiment, is incorporated in a sensitive layer 8 of sensitive material. The sensitive layer 8 fills the cavity 6 and projects from a plane P defined by a surface of the structural layer 3 opposite to the substrate 2. The sensor 1 is coated with a passivation layer 9. However, a free surface 8a of the sensitive layer 8, opposite to the substrate 2 is exposed and accessible from outside through a window 5 in the passivation layer 9.

The sensitive material is a material permeable to a volatile substance to be detected and has an electrical permittivity that depends upon the concentration of the volatile substance absorbed by the sensitive material itself. For instance, the electrical permittivity of the sensitive material increases as the concentration of the volatile substance absorbed increases. In one embodiment, the sensitive material is a hygroscopic polymeric material, in particular polyimide (PI), and the sensor 1 is a humidity sensor.

The sensing structure 7 comprises a first electrode structure 10 and a second electrode structure 11, which are capacitively coupled and are connected, respectively, to a first sensing terminal 1a and to a second sensing terminal 1b.

The capacitance between the first electrode structure 10 and the second electrode structure 11, which are incorporated in the sensitive layer 8, is at least in part determined by the electrical permittivity of the sensitive material, which depends upon the concentration of the volatile substance absorbed by the sensitive material and thus by its concentration in the surrounding environment.

The first electrode structure 10 and the second electrode structure 11 are arranged coplanar, for example in the plane P. In greater detail, the first electrode structure 10 comprises a plurality of electrodes 13 electrically connected together and to the first sensing terminal 1a by a connection line 12 so as to be maintained constantly equipotential. The electrodes 13 are defined by respective rectilinear conductive strips that extend parallel to one another in the plane P in a first direction D1. Likewise, the second electrode structure 11 comprises a plurality of electrodes 14 defined by respective rectilinear conductive strips, which extend parallel to one another and to the electrodes 13 in the plane P, in the first direction D1. Respective ends of the electrodes 14 are connected to the second sensing terminal 1b of the second electrode structure 11 through a connection line 16a.

In one embodiment, the electrodes 13 and the electrodes 14 are made of a refractory conductive material, for example an alloy of tantalum and aluminum substantially in equal parts. Alternatively, corrosion-resistant metals may be used, such as gold or platinum, or else again copper or aluminum. Refractory alloys and corrosion-resistant metals present the advantage of not being damaged by the presence of humidity. In other cases, the electrodes 13 and the electrodes 14 may be coated with a protective layer (not shown).

The electrodes 13 and the electrodes 14 are arranged in succession and alternated in an array in a second direction D2, perpendicular to the first direction D1, so that, except for the ends of the array, each electrode 13 is capacitively coupled to two adjacent electrodes 14 and, conversely, each electrode 14 is capacitively coupled to two adjacent electrodes 13. In one embodiment, the electrodes 13 and the electrodes 14 have the same width (W1, W2, respectively, with W1=W2) in the second direction D2; further, adjacent electrodes 13 and electrodes 14 are separated by a uniform spacing S.

Advantageously, the portions of the sensitive layer 8 comprised between the plane P and the bottom 6a of the cavities 6 and between the plane P and the free surface 8a have respective thicknesses T1, T2 approximately equal to the sum of the width W1, W2 of one of the layers 8, 9 and of the spacing S or thicker. Not necessarily are the thicknesses T1, T2 the same.

A supply device 15 is controlled by a control unit 17 and is selectively configured to cause a heating current $I_H$ to flow through the electrodes 14 of the second electrode structure 11 in a restoring operating condition and to interrupt the heating current $I_H$ at least in a sensing operating condition. The control unit 17 may be integrated in the same chip as that of the sensor 1 or else form part of an electronic system in which the sensor 1 is used.

In one embodiment, the supply device 15 comprises a supply source 18, for example a voltage generator, and a switch 19, controlled by the control unit 17. When the switch 19 is closed, it connects the electrodes 14 in parallel between terminals of the supply source 18 by the connection line 16a and a connection line 16b, enabling passage of the heating current $I_H$.

As already mentioned, the sensor 1 is coated with the passivation layer 9, which, through the window 5, leaves the free surface 8a exposed and accessible so that the environmental humidity (or the other substances to be detected) may impregnate the sensitive layer 8, modifying its electrical permittivity.

In the sensing operating condition, the supply device 15 is deactivated, and it is thus possible to detect the capacitance between the first electrode structure 10 and the second electrode structure 11 in a conventional way by measuring impedance between the first sensing terminal 1a and the second sensing terminal 1b.

At least in the restoring operating condition, the supply device 15 is activated by closing the switch 19. The supply source 18 causes the heating current $I_H$ to flow through the electrodes 14 of the second electrode structure 11, which, in this stage, heat up by the Joule effect and favor evaporation of the humidity or other substance to be detected absorbed by the sensitive layer 8.

In practice, then, a set of electrodes (here the electrodes 14 of the second electrode structure 11) are used both for detection of the humidity (or of some other substance sought) and as heaters in order to reduce the hysteresis of the sensor 1 and/or improve it sensitivity in conditions close to saturation.

The sensor according to the disclosure benefits from the presence of heaters, without, however, requiring integration of dedicated electrical components, and thus dedicated layers and machining steps. The structure and the manufacturing process are thus simplified. Furthermore, the heat is released directly by the sensing structure and, consequently, heating of the sensitive material is fast and uniform. Furthermore, the heaters in contact with the sensitive layer enable an improvement in the accuracy of the measurement for levels of relative humidity higher than 80% with satisfactory response times.

The distribution of the heat released may be easily determined in the design stage by selecting the number and dimensions of the electrodes. The heating current could be made to flow only through some of the electrodes of the second electrode structure, by selecting the connections to the supply source.

Figure 3:
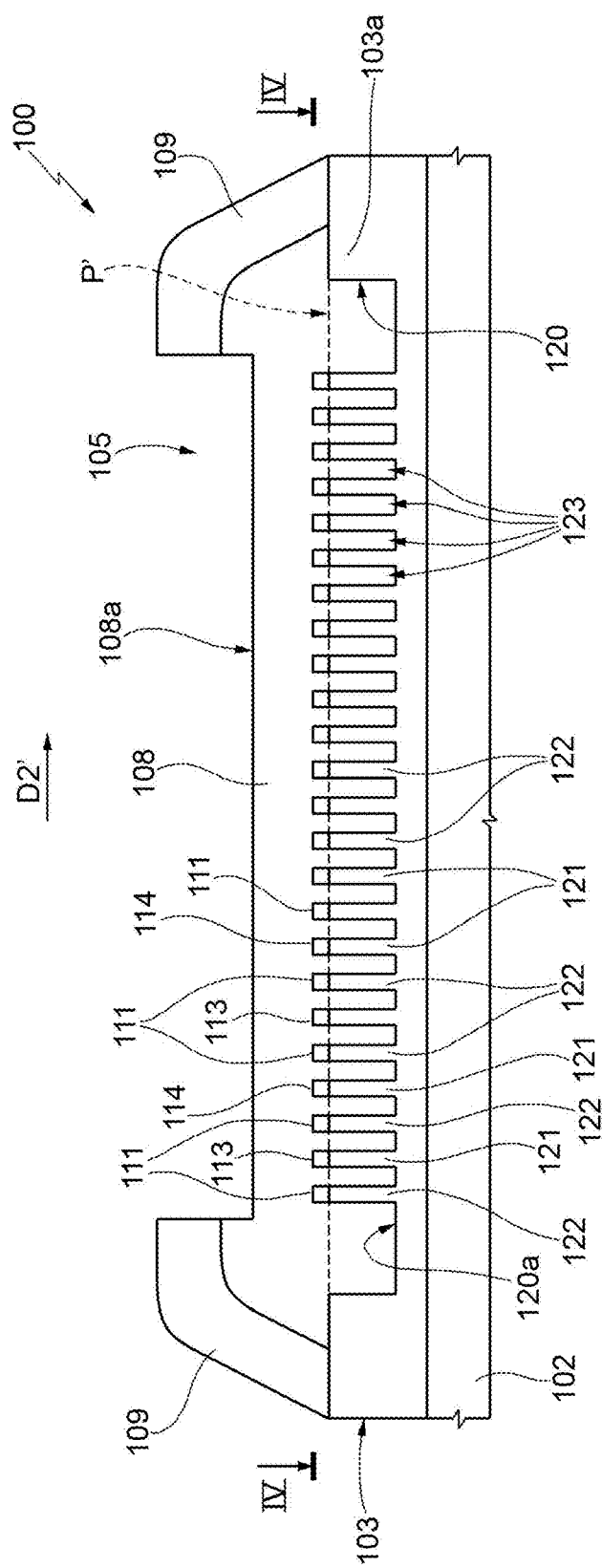
FIG. 3 is a cross-section through a sensor of volatile substances according to a different embodiment of the present disclosure.
Figure 4:
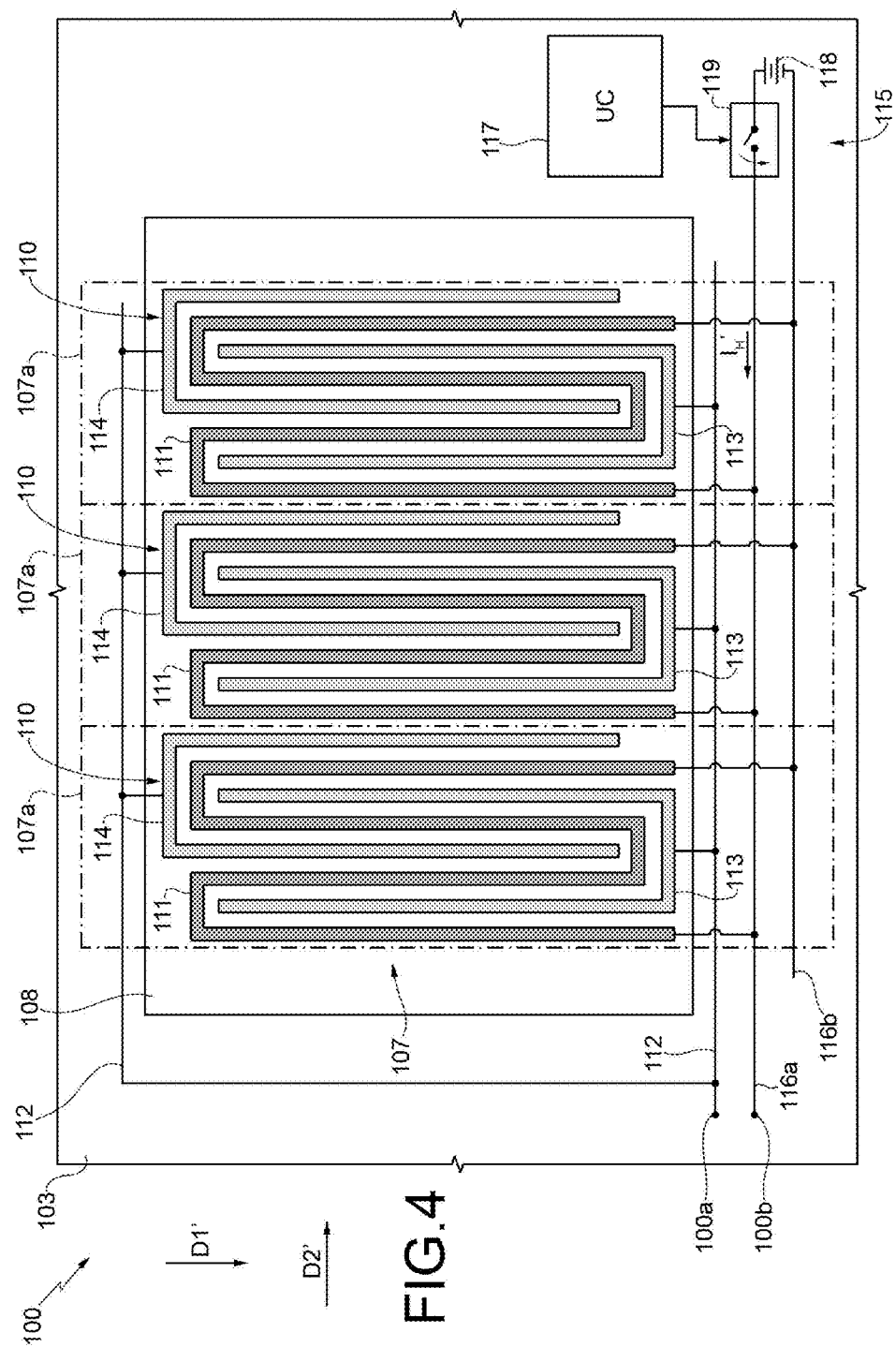
FIG. 4 is a simplified top plan view, with parts removed for reasons of clarity, of the sensor of FIG. 3, sectioned along the plane IV-IV of FIG. 3.

FIGS. 3 and 4 show a sensor of volatile substances 100 according to a different embodiment of the disclosure. The sensor 100 comprises a substrate 102, a structural layer 103 provided on the substrate 100, a sensing structure 107, and a sensitive layer 108 of sensitive material. The sensitive material is a material permeable to a volatile substance to be detected and has an electrical permittivity that depends upon the concentration of the volatile substance absorbed by the sensitive material itself. In particular, the sensitive material may be a hygroscopic material, for example polyimide; in this case, the sensor 100 is a humidity sensor.

The sensing structure 107 is planar and lies in a plane P' defined by a surface of the structural layer 103 opposite to the substrate 102.

In one embodiment, the sensing structure 107 is modular. Each module 107a comprises a first electrode structure 110 and a second electrode structure 111 capacitively coupled together and connected, respectively, to a first sensing terminal 100a and to a second sensing terminal 100b.

The first electrode structure 110 comprises a first electrode portion 113 and a second electrode portion 114, which are comb-shaped and comb-fingered. In greater detail, in the embodiment of FIGS. 3 and 4 the first electrode portion 113 and the second electrode portion 114 of each module 107a of the first electrode structure 110 each comprise two conductive strips that extend parallel in a first direction D1' and are joined by a respective back. The backs of the first electrode portion 113 and of the second electrode portion 114 are connected together and to the first sensing terminal by a connection line 112.

The second electrode structure 111 comprises a conductive strip, which extends along a serpentine path in a region comprised between the first electrode portion 113 and the second electrode portion 114 of the respective first electrode structure 110. Terminals at opposite ends of the second electrode structure 111 are connected, respectively, to a connection line 116a and to a connection line 116b distinct from one another. The connection line 116a is in turn connected to the second sensing terminal 100b.

The modules 107a of the sensing structure 107 are set in succession in a second direction D2', perpendicular to the first direction D1'. In one embodiment, the connection lines 112, 116a, 116b extend in the second direction D2'.

The sensing structure 107 is supported by the structural layer 103. In greater detail, the structural layer 103 comprises an external frame 103a, which delimits a cavity 120, and a first supporting structure 121 and a second supporting structure 122 in the cavity 120. The first supporting structure 121 and the second supporting structure 122 rise from a bottom surface 120a of the cavity 120 up to a surface of the structural layer 103 opposite to the substrate 102 and support, respectively, the first electrode structure 110 and the second electrode structure 111 of each module of the sensing structure 107. The first supporting structure 121 is defined by walls corresponding in shape to respective first portions of electrode 113 and second portions of electrode 114 of the first electrode structures 110. The second supporting structure 122 is defined by walls corresponding in shape to respective second electrode structures 111.

The first supporting structure 121 and the second supporting structure 122 define between them recesses 123 that extend from the bottom surface 120a of the cavity 120 up to the surface of the structural layer 103 that defines the plane P'.

The sensitive layer 108 fills the cavity 120 and the recesses 123 and projects out of them. The sensitive layer 108 thus extends on both sides of the plane P', precisely between the plane P' and the bottom surface of the cavity 120 and of the recesses 123 and between the plane P' and a free surface 108a.

A supply device 115 is controlled by a control unit 117 and is selectively configured to cause a heating current $I_H'$ to flow through the second electrode structures 111 in a restoring operating condition and to interrupt the heating current $I_H'$ at least in a sensing operating condition. The control unit 117 may be integrated in the same chip as that of the sensor 100 or else form part of an electronic system in which the sensor 100 is used.

In one embodiment, the supply device 115 comprises a supply source 118, for example a voltage generator, and a switch 119, controlled by the control unit 117. When the switch 119 is closed, it connects the supply source 118 between the connection line 116a and the connection line 116b, enabling passage of the heating current $I_H'$ along the second electrode structures 111 of the sensing structure 107.

The sensor 100 is finally coated with a passivation layer 109, which has a window 105 for access to the sensitive layer 108. The window 105 leaves the free surface 108a exposed and accessible so that the substance or substances to be detected may impregnate the sensitive layer 108, modifying its electrical permittivity.

Figure 5:
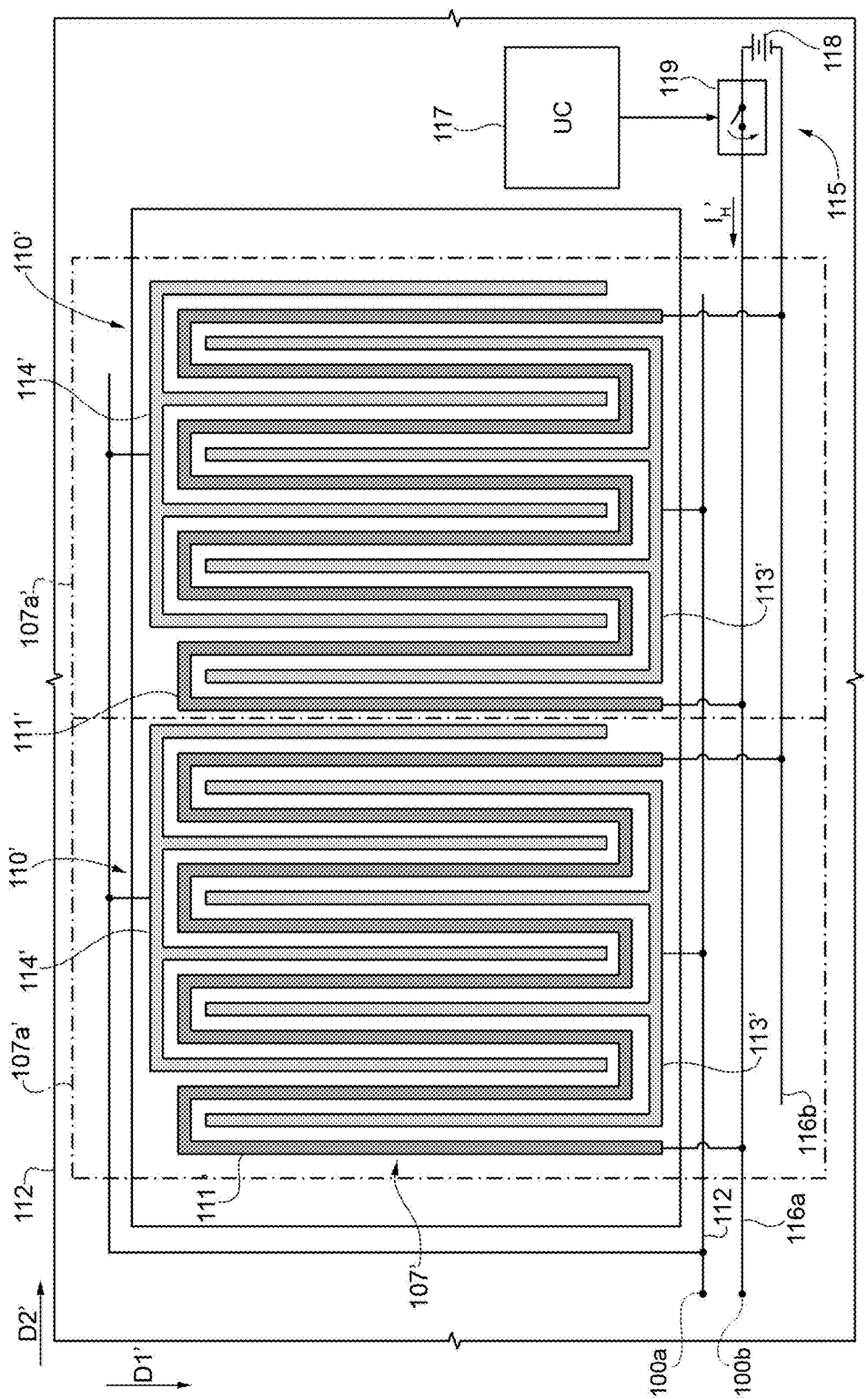
FIG. 5 is a simplified top plan view, with parts removed for reasons of clarity, of a sensor of volatile substances according to another embodiment of the present disclosure.

The embodiment illustrated in FIG. 5 differs from the previous one in that, in each module 107a' of the sensing structure 107', the first portions of electrode 113' and the second portions of electrode 114' of the first electrode structures 110' each comprise more than two parallel conductive strips, for example four. The first portions of electrode 113' and the second portions of electrode 114' of the first electrode structures 110' are comb-fingered as in the previous case, and the second electrode structures 111' extend along a serpentine path in the space between the respective first portions of electrode 113' and second portions of electrode 114'.

The sensing structure may also comprise a single module, with just one first electrode portion and just one second electrode portion that form the first electrode structure.

According to a different embodiment (illustrated in FIGS. 6 and 7), a sensor of volatile substances 200 comprises a substrate 202, a structural layer 203 on the substrate 202, a sensing structure 207, and a sensitive layer 208 of a sensitive material. The sensitive material is a material permeable to a volatile substance to be detected and has an electrical permittivity that depends upon the concentration of the volatile substance absorbed by the sensitive material itself, for example a hygroscopic material such as polyimide; in this case, the sensor 200 is a humidity sensor.

The sensing structure 207 is planar and lies in a plane P'" defined by a surface of the structural layer 203 opposite to the substrate 202. Furthermore, the sensing structure 207 is incorporated in the sensitive layer 208. In particular, the structural layer 203 has a through cavity 206, the bottom 206a of which is defined by a surface of the underlying layer, in this case the substrate 202. The cavity 206 is occupied by a portion of the sensitive layer 208, a further portion of which extends on the opposite side of the sensing structure 207 as far as a free surface 208a.

In greater detail, the sensing structure 207 comprises a first electrode structure 210 and a second electrode structure 211, which are capacitively coupled together and connected, respectively, to a first sensing terminal 200a and to a second sensing terminal 200b (FIG. 6).

The first electrode structure 210 comprises a plurality of electrodes 213, each of which has a respective conductive strip 213a that extends in a first direction D1" (FIG. 7) and a plurality of conductive strips 213b that extend on opposite sides of the respective conductive strip 213a in a second direction D2" perpendicular to the first direction D1". The conductive strips 213b are evenly spaced in the first direction D1". The electrodes 213 are electrically connected together and to the first sensing terminal 200a by a connection line 212 so as to be kept constantly equipotential.

The second electrode structure 211 comprises a plurality of electrodes 214, each of which has a respective conductive strip 214a that extends in the first direction D1" and a plurality of conductive strips 214b that extend on opposite sides of the respective conductive strip 214a in the second direction D2". The conductive strips 214b are evenly spaced in the first direction D1". The electrodes 214 at the ends of the sensing structure 207 have conductive strips 214b only on one side of the respective conductive strip 214a, precisely towards the inside of the sensing structure 207.

The conductive strips 213b and the conductive strips 214b of adjacent electrodes 213, 214 are comb-fingered.

The ends of the second electrode structure 211 are connected, respectively, to a connection line 216a and to a connection line 216b. The connection line 216a is in turn connected to the second sensing terminal 200b.

A supply device 215 is controlled by a control unit 217 and is selectively configured to get a heating current $I_H$" to flow through the electrodes 214 of the second electrode structure 211 in a restoring operating condition and for interrupting the heating current $I_H$" at least in a sensing operating condition. The control unit 217 may be integrated in the same chip as that of the sensor 200 or else form part of an electronic system where the sensor 200 is used.

In one embodiment, the supply device 215 comprises a supply source 218, for example a voltage generator, and a switch 219, controlled by the control unit 217. When the switch 219 is closed, it connects the supply source 218 between the connection line 216a and the connection line 216b, enabling passage of the heating current $I_H$" along the second electrode structures 211 of the sensing structure 207.

The sensor 200 is finally coated with a passivation layer 209, which has a window 205 for access to the sensitive layer 208. The window 205 leaves the free surface 208a exposed and accessible so that the substance or substances for being detected may impregnate the sensitive layer 208, modifying its electrical permittivity.

Figure 7:
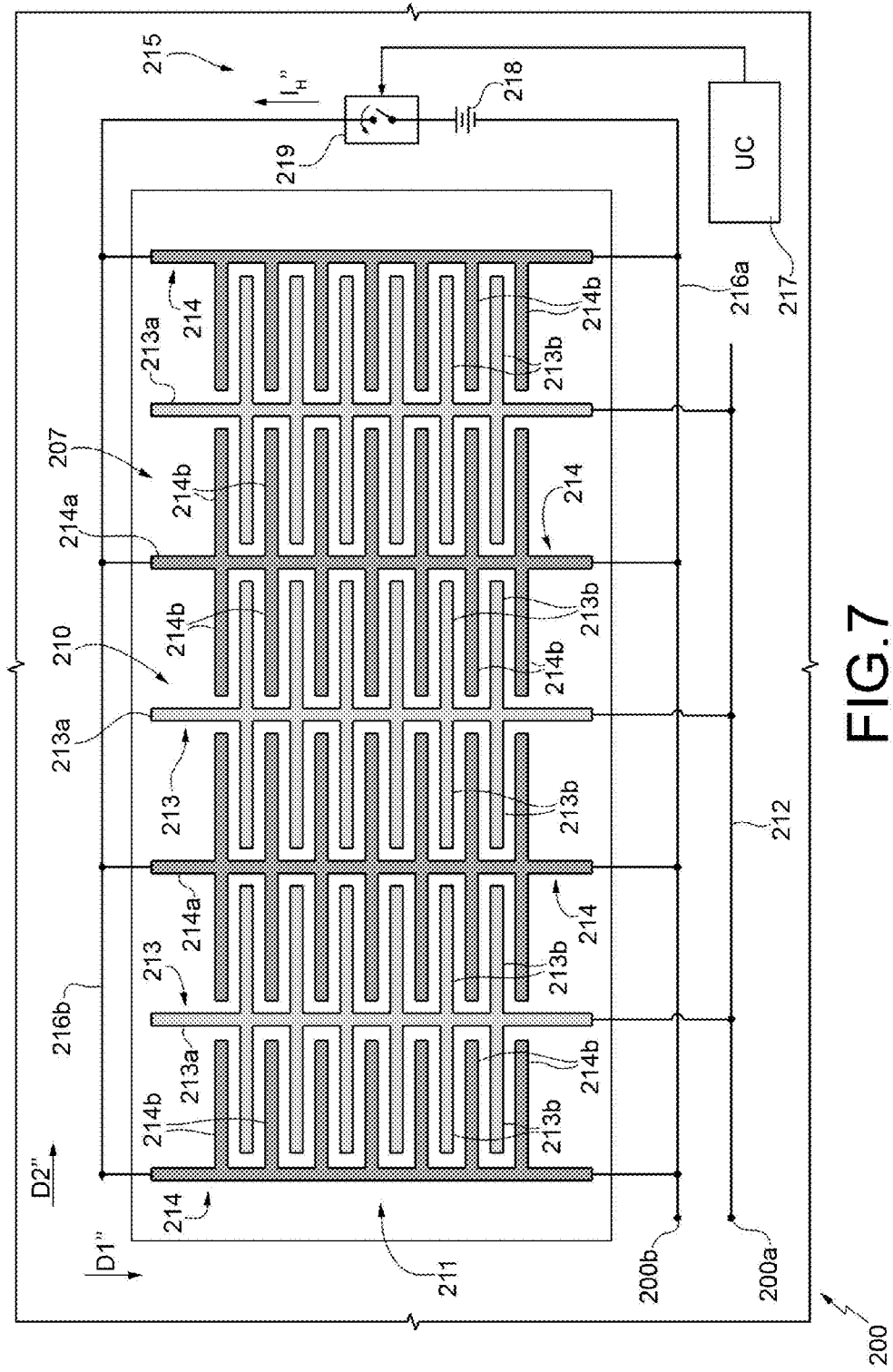
FIG. 7 is a simplified top plan view, with parts removed for reasons of clarity, of the sensor of FIG. 6, sectioned along the plane VII-VII of FIG. 6.
Figure 9:
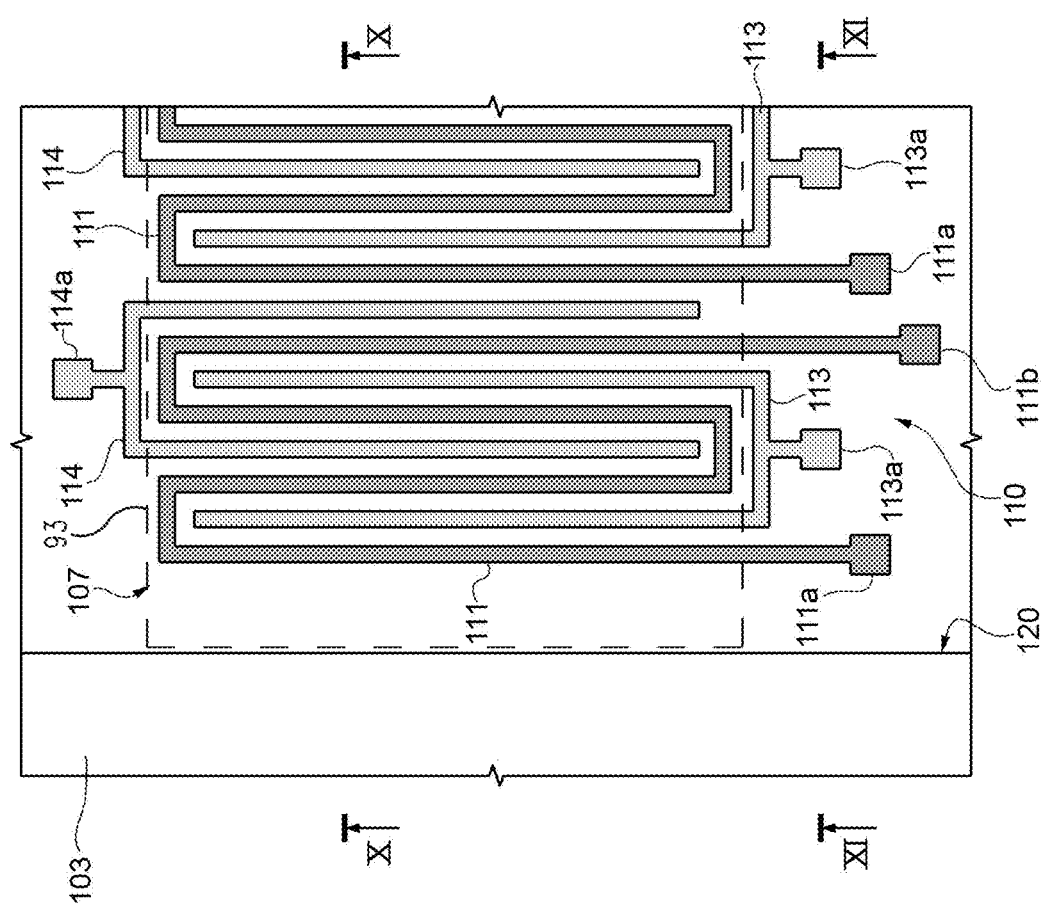
FIG. 9 is a simplified top plan view, with parts removed for reasons of clarity, of a semiconductor wafer after initial steps of a process for manufacturing a sensor of volatile substances according to one embodiment of the present disclosure.

In the embodiment of FIGS. 6 and 7, the heating current basically flows along the conductive strips 214a of the electrodes 214. The heat here generated by the Joule effect propagates by conduction through the conductive strips 214b. The selection of the dimensions of the electrodes 214 (length, width, and thickness of the conductive strips 214a, 214b) allows to obtain a substantially uniform heating of the sensitive layer 208.

With reference to FIG. 8, a sensor of volatile substances 200' according to a different embodiment of the disclosure differs from the sensor 200 of FIGS. 6 and 7 in that the sensing structure 207 lies on a structural layer 203', for example a silicon-oxide layer, that is substantially continuous and without any cavities. In this case, a sensitive layer 208' coats the sensing structure 207 only on one side. The sensitive layer 208' is made of a sensitive material, which is permeable to a volatile substance to be detected and has an electrical permittivity depending upon the concentration of the volatile substance absorbed.

The sensor of volatile substances according to the disclosure, in particular the sensor 100 of FIG. 3, may be manufactured as described hereinafter with reference to FIGS. 9-18.

Initially (FIGS. 9-11), the structural layer 103 is grown on the substrate 102 by thermal oxidation. A layer of conductive material (not shown entirely) is deposited on the structural layer 103, for example by sputtering, and subsequently defined by a photolithographic process to obtain the sensing structure 107 and the contact pads 113a, 114a. The deposited material may be refractory conductive material, for example an alloy of tantalum and aluminum, or else a non-alloy metal, such as gold, platinum, silver, copper, or aluminum.

In this step, a resist mask 130 is used for forming the first electrode structures 110 (with the respective first portions of electrode 113 and second portions of electrode 114) and the second electrode structures 111. Furthermore, the same resist mask 130 enables also formation of contact pads 113a, 114a (see a contact pad region 95 in FIG. 11), respectively, for the first portions of electrode 113 and the second portions of electrode 114 and contact pads 111a, 111b at respective ends of each second electrode structure 111.

After the electrodes are defined by the resist mask 130, the resist mask is removed. A dedicated photomask 91 is formed to form the cavities. The photomask 91 protects and covers the contact pad region 95, see FIG. 11a.

Figure 10A:
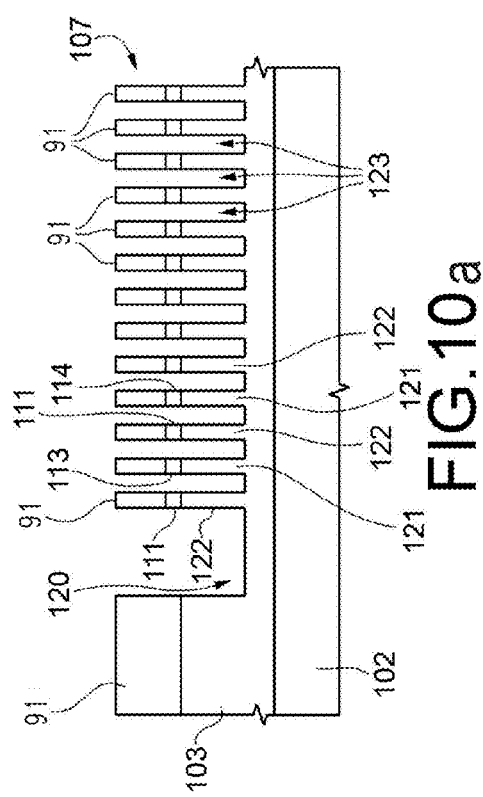
FIG. 10a shows the view of FIG. 10 in a subsequent machining step.
Figure 11A:
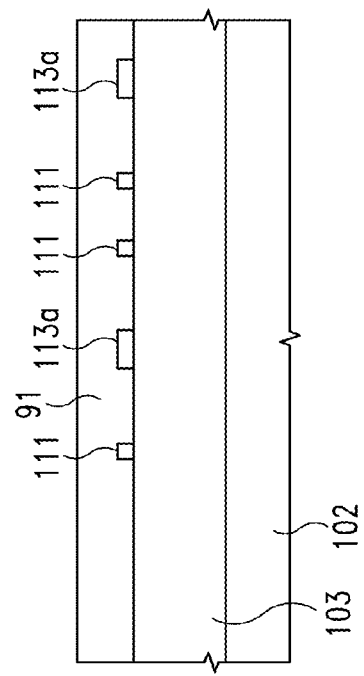
FIG. 11a shows the view of FIG. 11 in a subsequent machining step.

A time-controlled dry etch of the structural layer 103 is then carried out to form the cavity 120 and the serpentine recesses 123 and to define the first supporting structure 121 and the second supporting structure 122, see FIG. 10a. The time-controlled etch is performed in a sensing structure region 93, see dashed lines in FIG. 9. No cavities are formed in the contact pad region 95, see FIG. 11a. The contact pad region 95 is covered by the photomask 91 while the cavities are formed in the sensing structure region 93.

In FIGS. 12 and 13, the sensitive material is deposited on the wafer and exposed to light to form the sensitive layer 108 in the sensing region 93. The portions of the sensing layer 108 not in the sensing region 93 are removed. The sensing layer 108 is totally removed from the pad region 95. After the sensitive layer 108 has been deposited and it is exposed to light, if necessary, and undergoes a curing step. Then, a first passivation layer 109a, for example silicon nitride, is deposited.

As shown in FIGS. 14 and 15, the first passivation layer 109a is then selectively etched using a photolithographic process to obtain contact windows 131 above the pads 111a, 111b, 113a, 114a (in FIG. 15, only some pads 113a are visible).

Next, a metallization layer 132 is deposited (shown with a dashed line in FIG. 14), which contacts the pads 111a, 111b, 113a, 114a through the contact windows 131. The metallization layer 132 is defined by a further photolithographic process for forming the connection lines 112, 116a, 116b (as is shown more clearly in FIG. 16; in FIG. 15 only one portion of connection line 112 that contacts the pads 113a is visible). The electrical connection lines 116a, 116b are connected together through each second electrode structure 111.

After the connection lines 112, 116a, 116b have been defined, a second passivation layer 109b (FIGS. 17 and 18) is deposited. Then, the passivation layer 109, which, above the sensitive layer 108, is formed by the first passivation layer 109a and by the second passivation layer 109b, is selectively etched by a further photolithographic process for opening the window 105 for access to the sensitive layer 108.

Once the operations of dicing have been carried out, the sensor 100 illustrated in FIG. 3 is obtained.

Finally, it is evident that modifications and variations may be made to the sensor and to the process described herein, without thereby departing from the scope of the present disclosure.

In particular, it is understood that all the sensing structures described may be indifferently incorporated in the sensitive layer (as in the embodiments of FIGS. 1, 2 and 6), or else be made on supporting structures with recesses that enable the sensitive material to be laid on both sides of the sensing structure (as in the embodiment of FIGS. 3 and 4), or else again be arranged on a continuous structural layer, with the sensitive material in practice only on one side of the sensing structure (as in the embodiment of FIG. 8).

The form of the electrode structures may both as regards dimensions and shape, at the same time guaranteeing that the first electrode structures and the second electrode structures are capacitively coupled so that the capacitance is affected by the electrical permittivity of the sensitive material.

Furthermore, the first electrode structures or the second electrode structures are provided with terminals for connection to the supply device for being used as heaters.

The supply device may be incorporated in the chip of the sensor or else be external, as likewise the control unit.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
a substrate;
a sensitive layer on the substrate, wherein the sensitive layer is permeable to a volatile substance to be detected and has an electrical permittivity that depends on a concentration of the volatile substance absorbed;
a first electrode structure on the sensitive layer, the first electrode structure includes a first electrode finger, a second electrode finger, and a third electrode finger that are coupled together;
a second electrode structure on the sensitive layer, the second electrode structure having a serpentine shape, the second electrode structure being capacitively coupled to the first electrode finger and to the second electrode finger;
a third electrode structure capacitvely coupled to the second electrode structure, the sensitive layer being between the first electrode structure, the second electrode structure, and the third electrode structure, the third electrode structure having a fourth electrode finger capacitively coupled to the second electrode finger and the third electrode finger, wherein the first, second, and third electrode structures are coplanar; and
a supply device configured to couple a heating current to the first electrode structure to transfer heat to the sensitive layer, while the second electrode structure and the third electrode structure remain uncoupled from the heating current of the supply device.

2. The device according to claim 1, wherein the sensitive layer is made of a hygroscopic polymer.

3. The device according to claim 1 wherein the first, second and third electrode fingers of the first electrode structure extend away from a first extension that is transverse to the first, second and third electrode fingers.

4. The device according to claim 1 wherein the second electrode structure is consistently spaced from the first, second and third electrode fingers of the first electrode structure.

5. A device, comprising:
a substrate;
a sensitive layer on the substrate;
a first electrode structure on the sensitive layer, the first electrode structure includes a first electrode finger, a second electrode finger, and a third electrode finger that are coupled together;
a second electrode structure on the sensitive layer, the second electrode structure having a serpentine shape, the second electrode structure being capacitively coupled to the first electrode finger and to the second electrode finger, the sensitive layer being between the first electrode structure and the second electrode structure;
a third electrode structure on the sensitive layer, the third electrode structure having a fourth electrode finger capacitively coupled to the second electrode finger and the third electrode finger, the first, second, and third electrode structures being coplanar; and
a supply device configured to couple a heating current through the first, second, and third electrode fingers of the first electrode structure in a first operating condition to heat the sensitive layer, the second and third electrode structures remaining uncoupled from the heating current of the supply device.

6. The device according to claim 5 wherein the first, second and third electrode fingers of the first electrode structure extend away from a first extension that is transverse to the first, second and third electrode fingers.

7. The device according to claim 6 wherein the second electrode structure is consistently spaced from the first, second and third electrode fingers of the first electrode structure.

8. A device, comprising:
a substrate;
a cavity in the substrate;
a hygroscopic polymer in the cavity;
a first electrode structure on a plane in the cavity, the first electrode structure having a first plurality of electrode fingers;
a second electrode structure on the plane in the cavity, the second electrode structure having a second plurality of electrode fingers, the first plurality of electrode fingers extending between the second plurality of electrode fingers;
a third electrode structure on the plane in the cavity, the third electrode structure having a serpentine shape that is positioned between adjacent ones of the first and second pluralities of electrode fingers; and
a supply device configured to couple a heating current to the first electrode structure to transfer heat to the hygroscopic polymer, while the second electrode structure and the third electrode structure remain uncoupled from the heating current of the supply device.

9. The device of claim 8 wherein each of the first and second electrode structures are U-shaped.

10. The device of claim 9 wherein each of the U-shaped first and second electrode structures includes a base and a first and second prong that extend away from the base.

11. The device of claim 10 wherein the third electrode structure includes a first end positioned adjacent to the base of the first electrode structure and a second end positioned adjacent to the base of the second electrode structure.

12. The device of claim 11 wherein the third electrode structure is consistently spaced from the first electrode structure and the second electrode structure.

* * * * *